United States Patent [19]

Foster

[11] 4,075,226
[45] Feb. 21, 1978

[54] SECONDARY ANTIOXIDANTS
[75] Inventor: Charles H. Foster, Kingsport, Tenn.
[73] Assignee: Eastman Kodak Company, Rochester, N.Y.
[21] Appl. No.: 777,236
[22] Filed: Mar. 11, 1977
[51] Int. Cl.$^2$ .................. C07D 335/04; C07D 497/20
[52] U.S. Cl. ............................................. 260/327 TH
[58] Field of Search ............................... 260/327 TH
[56] References Cited
U.S. PATENT DOCUMENTS
3,966,815  6/1976  Freed et al. ..................... 260/570.8
4,000,112  12/1976  Stephen ...................... 260/45.8 RW Primary Examiner—Cecilia M. S. Jaisle
Attorney, Agent, or Firm—Elliott Stern; Daniel B. Reece, III

[57] ABSTRACT

Decahydro-3,3,8,8-tetramethoxy-2,7-epithio-1,4-ethanonaphthalene-5,9-dione, decahydro-3,3,8,8-tetraethoxy-2,7-epithio-1,4-ethanonaphthalene-5,9-dione, decahydro-dispiro[1,3-dioxolane-2,3'-(2',7'-epithio-1',4'-ethanonaphthalene)-8',2''-[1,3]dioxolane]-5',9'-dione have been found to be effective as secondary antioxidants for polyolefins.

3 Claims, No Drawings

SECONDARY ANTIOXIDANTS

This invention relates to novel compositions of matter, decahydro-3,3,8,8-tetramethoxy-2,7-epithio-1,4-ethanonaphthalene-5,9-dione (I), decahydro-3,3,8,8-tetraethoxy-2,7-epithio-1,4-ethanonaphthalene-5,9-dione (II), and decahydro-dispiro[1,3-dioxolane-2,3'-(2',7'-epithio-1',4'-ethanonaphthalene)-8',2''-[1,3]dioxolane]-5',9'-dione (III), which are useful as secondary antioxidants in polyolefins. The compounds of this invention have been found useful in polyolefins such as polypropylene, polyethylene, and the like. For example, samples of polypropylene treated with 0.5% of Compound I in addition to the primary antioxidant dioctadecyl-p-cresol, gave an oven life at 150° C. of 340 hours versus 35 hours when the primary antioxidant alone was used.

These compounds can be used in conjunction with primary antioxidants such as bis(methylheptadecyl)-p-cresol, di-t-butyl-p-cresol, and other well known primary antioxidants.

The following examples show how the compounds of this invention may be prepared.

EXAMPLE 1

Preparation of decahydro-3,3,8,8-tetramethoxy-2,7-epithio-1,4-ethanonaphthalene-5,9-dione.

A. A solution of $Na_2S.9H_2O$ (4.8 g., 0.02 mol.) in $H_2O$ (10 ml.) was added to a stirred mixture of 4,4-dimethoxycyclohexa-2,5-dienone prepared by the procedure of Nilsson et al, *Tetrahedron Lett.*, 1107 (1975) (3 g., 0.02 mol.) and $H_2O$ (40 ml.) at 10° C. The mixture was stirred at 10° C. for 2 hours. The ice bath was removed and stirring continued at room temperature 48 hrs. The product precipitated and was isolated by filtration, washed with $H_2O$ and dried (1.44 g., 42% yield). Recrystallization from ethanol gave a sample which melted at 201°–205° C. but on solidification and remelting gave m.p. 201°–203° C. The ir spectra of the initial and melted samples were identical: ir (KBr) 1727, 1700, 1111, 1064, 1046 $cm^{-1}$; $^1H$ NMR ($CDCl_3$) δ 3.28 (s, 3H), 3.24 (s, 6H), 3.16 (s, 3H), 3.14–1.9 (m, 10 H); $^{13}C$ NMR ($CDCl_3$) 209.5, 208.4, 101.0, 97.1, 51.1, 49.7, 48.4, 48.3, 47.6, 46.1, 44.7, 42.4, 40.7, 39.4, 36.7, 31.9; mass spectrum m/e 342 (M), 101, 91, 75, 59, 55.

Anal. Calcd. for $C_{16}H_{22}O_6S$: C, 56.12; H, 6.48; S, 9.37. Found: C, 56.34; H, 6.40; S, 9.33.

Preparation of intermediate 4,4-dimethoxycyclohexa-2,5-dienone.

The procedure of Nilsson et al was generally followed: p-methoxyphenyl (20 g.) dissolved in methanol (120 ml.) containing lithium perchloate (8 g.) was stirred magnetically and subjected to constant current (2.0 A) electrolysis at a cell voltage of about 25 V on a platinum anode (50 $cm^2$) in an open water-cooled (10° C.) vessel. The cathode was a 6 cm. length of copper wire (diameter 0.7 mm.). The oxidation was monitored by NMR or VPC. When 95–100% of the starting material had been consumed (this requires about 3.6 Faradays/mol., corresponding to an electrolysis time of about 8 hours), the electrolysis mixture was poured into a phosphate buffer (pH 6, 600 ml.). Extraction with dichloromethane (3 × 150 ml.) followed by evaporation at reduced pressure (the temperature of the heating bath should not exceed 30° C.) gave crude 2 (24 g.). Further purification can be achieved by filtration through neutral alumina (Woelm Dry Column, Activity III, ethyl acetate eluent) or by distillation at reduced pressure but decomposition of the dienone reduces the yield substantially on distillation.

EXAMPLE 2

Decahydro-3,3,8,8-tetraethoxy-2,7-epithio-1,4-ethanonaphthalene-5,9-dione, and decahydro-dispiro[1,3-dioxolane-2,3'-(2',7'-epithio-1',4'-ethanonaphthalene)-8',2''-[1,3]dioxolane]-5',9'-dione were made in accordance with the procedure set forth in Example 1 except that the corresponding ketals are utilized instead of 4,4-dimethoxycyclohexa-2,5-dienone.

The invention has been described in detail with particular reference to certain preferred embodiments thereof, but it will be understood that variations and modifications can be effected within the spirit and scope of the invention.

I claim:
1. Decahydro-3,3,8,8-tetramethoxy-2,7-epithio-1,4-ethanonaphthalene-5,9-dione.
2. Decahydro-3,3,8,8-tetraethoxy-2,7-epithio-1,4-ethanonaphthalene-5,9-dione.
3. Decahydro-dispiro[1,3-dioxolane-2,3'-(2',7'-epithio-1',4'-ethanonaphthalene)-8',2''-[1,3]dioxolane]-5',9'-dione.

* * * * *